US010228280B2

(12) United States Patent
Abel et al.

(10) Patent No.: US 10,228,280 B2
(45) Date of Patent: Mar. 12, 2019

(54) OPTICAL SENSOR

(71) Applicant: International Business Machines Corporation, Armonk, NY (US)

(72) Inventors: Stefan Abel, Zurich (CH); Jean Fompeyrine, Waedenswil (CH); Antonio La Porta, Kilchberg (CH)

(73) Assignee: International Business Machines Corporation, Armonk, NY (US)

( * ) Notice: Subject to any disclaimer, the term of this patent is extended or adjusted under 35 U.S.C. 154(b) by 206 days.

(21) Appl. No.: 15/428,511

(22) Filed: Feb. 9, 2017

(65) Prior Publication Data

US 2018/0224327 A1 Aug. 9, 2018

(51) Int. Cl.
| | | |
|---|---|---|
| *G01J 1/44* | (2006.01) | |
| *G01N 21/05* | (2006.01) | |
| *G01N 21/03* | (2006.01) | |
| *G01N 15/00* | (2006.01) | |
| *G01N 21/47* | (2006.01) | |

(52) U.S. Cl.
CPC ............. *G01J 1/44* (2013.01); *G01N 15/00* (2013.01); *G01N 21/0303* (2013.01); *G01N 21/05* (2013.01); *G01N 21/47* (2013.01); *G01N 2021/4711* (2013.01); *G01N 2021/4719* (2013.01); *G01N 2201/08* (2013.01); *G01N 2201/12* (2013.01); *G01N 2201/1296* (2013.01)

(58) Field of Classification Search
CPC .......... G01J 1/44; G01N 15/00; G01N 21/47; G01N 21/0303; G01N 21/05; G01N 2201/1296; G01N 2021/4719; G01N 2021/4711; G01N 2201/08; G01N 2201/12

USPC ........................................ 250/214.1; 359/107
See application file for complete search history.

(56) References Cited

U.S. PATENT DOCUMENTS

| | | | |
|---|---|---|---|
| 8,288,157 B2 | 10/2012 | Duer | |
| 8,582,108 B2 | 11/2013 | Walters | |
| 8,588,557 B2 | 11/2013 | Schmidt et al. | |
| 9,165,246 B2 * | 10/2015 | Pickett | G11C 11/54 |
| 9,291,568 B2 | 3/2016 | McCaffrey et al. | |
| 9,310,300 B2 | 4/2016 | Alt et al. | |

(Continued)

FOREIGN PATENT DOCUMENTS

WO WO2013/046752 A1 3/2016

OTHER PUBLICATIONS

Georg Pucker et al., An Integrated Optical Biosensor Platform, SPIE Newsroom, SPIE Mar. 21, 2016, pp. 1-3.

(Continued)

*Primary Examiner* — Seung C Sohn
(74) *Attorney, Agent, or Firm* — Daniel P. Morris; Otterstedt, Ellenbogen & Kammer, LLP

(57) ABSTRACT

An optical sensor includes an interaction region configured to comprise an analyte and an illumination source configured to illuminate the interaction region with an optical input signal. The optical sensor further includes an optical coupling structure configured to collect transmitted parts of the optical input signal from the interaction region and an optical neuromorphic network that is directly optically coupled to the optical coupling structure and is configured to receive and process the transmitted parts of the optical input signal in the optical domain. The invention further concerns a related method for analyzing an analyte by an optical sensor.

19 Claims, 6 Drawing Sheets

(56) References Cited

U.S. PATENT DOCUMENTS 9,477,136 B2 * 10/2016 Bienstman ........... G06N 3/0675

OTHER PUBLICATIONS

Kristof Vandoorne et al., . Experimental Demonstration of Reservoir Computing on a Silicon Photonics Chip, Nature Communications 5, Article No. 3541, Published Mar. 24, 2014, pp. 1-12.
Kristof Vandoorne et al., Advances in Photonic Reservoir Computing on an Integrated Platform, IEEE ICTON 2011, pp. 1-4.
Lin Luan et al., Integrated Optical Sensor in a Digital Microfluidic Platform, IEEE Sensors Journal • V8N5 May 2008, pp. 628-635.
Stefan Abel, et al., unpublished U.S. Appl. No. 15/859,424, filed Dec. 30, 2017, Optical Sensor, pp. 1-25 plus 6 sheets of drawings.
Paul J. Otterstedt, List of IBM Patents or Patent Applications Treated as Related, Jun. 21, 2018, pp. 1-2.

* cited by examiner

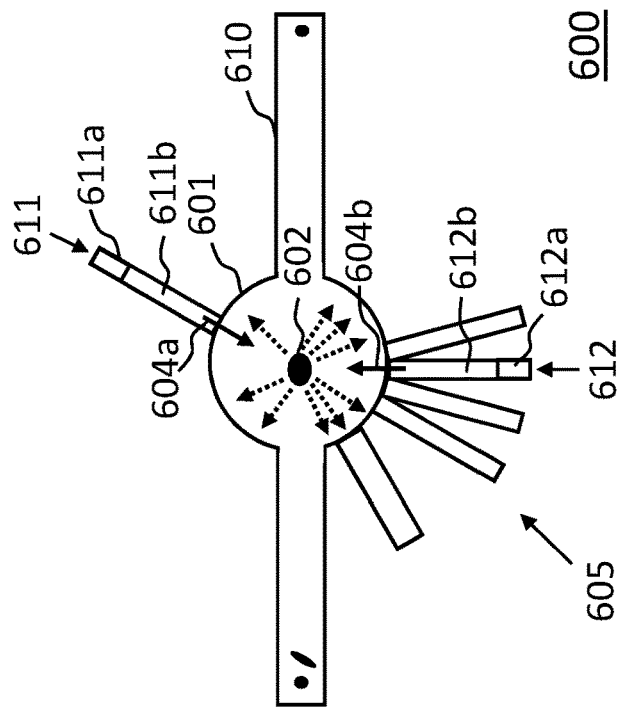
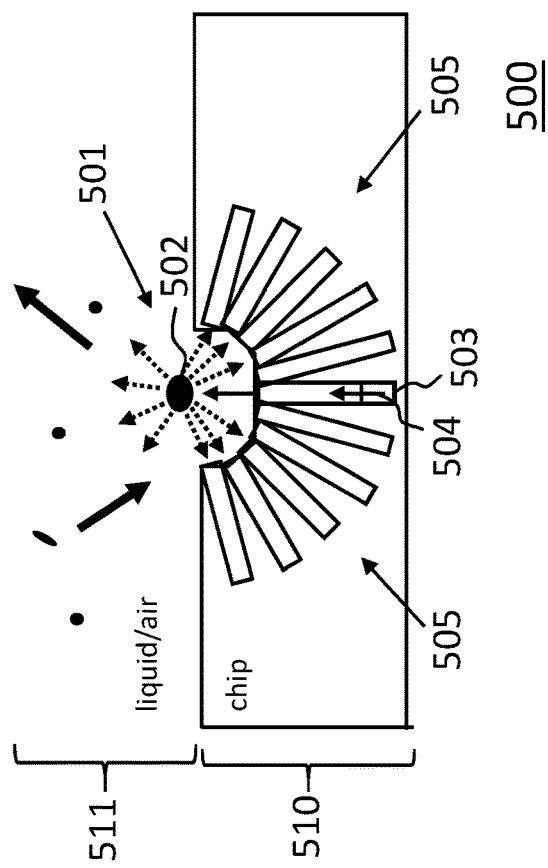
FIG. 6
FIG. 5

OPTICAL SENSOR

BACKGROUND

The present invention relates generally to an optical sensor for analyzing an analyte, in particular for detecting elements such as particles in liquids or gases, liquids, gases and/or plasma.

The invention also relates to a corresponding method for analyzing an analyte.

Optical sensors to detect chemical substances and small particles are e.g. used for analyzing gases, contaminants in liquids or biological particles. These sensors are often very bulky and may comprise e.g. large laser systems and mechanical components. Accordingly, they are often driven by significant power levels and hence not well suited for small sensors as desired for example in the field of Internet of Things.

Such optical sensors usually comprise a light source and corresponding optics to illuminate the sample. Then scattered, transmitted and/or absorbed light is detected, converted in the electrical domain and electrically processed for determining the desired information.

Accordingly, there is a need for other optical sensors.

SUMMARY

According to a first aspect, the invention is embodied as an optical sensor comprising an interaction region configured to comprise an analyte and an illumination source configured to illuminate the interaction region with an optical input signal. The optical sensor further comprises an optical coupling structure configured to collect transmitted parts of the optical input signal from the interaction region and an optical neuromorphic network being directly optically coupled to the optical coupling structure and being configured to receive and process the transmitted parts of the optical input signal in the optical domain.

Hence, according to embodiments, the optical neuromorphic network can perform at least a part of the processing for the analysis/detection in the optical domain. This facilitates the design of detection and analysis systems that may provide advantages in particular in terms of speed, accuracy and power consumption. Furthermore, it may facilitate the design of compact sensor systems.

The term transmitted parts of the optical input signal shall encompass all parts of the optical input signal that can be collected by the optical coupling structure. This encompasses scattered, reflected and/or distracted parts of the optical input signal. The transmitted parts of the optical input signal shall also include any kind of changes to the optical input signal that may occur due to any interaction of the optical input signal with the analyte such as phase changes, frequency changes, or optical absorption. Furthermore, the transmitted parts of the optical input signal may also comprise changes to the optical input signal that may occur as a result of an interaction of the analyte with the interaction region itself, e.g. with the surface of the interaction region. The latter may also change the optical transmission characteristics of the interaction region.

The term analyte shall be understood in a broad sense to denote any kind of analytes or combinations of analytes that can be analyzed, in particular detected, by an optical sensor, e.g. particles, molecules, gases, plasma, chemical substances, contaminants in liquids, biological particles, etc.

According to an embodiment, the optical neuromorphic network is configured to be trained on performing a classification of the analyte.

The classification may be done according to embodiments with low latency. Furthermore, according to such an embodiment, the neuromorphic network may be trained specifically to the respective targeted application. As an example, according to one embodiment, the neuromorphic network may be trained to just distinguish two sets of gases with high precision, while according to another embodiment the neuromorphic network may be trained to distinguish e.g. 10 sets of gases with lower precision.

According to an embodiment, the optical neuromorphic network is configured to be trained on performing a forecasting of one or more properties of the analyte. Such a forecasting/prediction may be e.g. the forecast that a gas concentration will exceed a predetermined threshold within a predetermined amount of time.

According to an embodiment, the optical neuromorphic network is an optical reservoir system.

According to an embodiment, the optical reservoir system comprises a plurality of optical reservoir nodes and a plurality of optical reservoir connections between the plurality of optical reservoir nodes.

Such an embodied neuromorphic network operates as a reservoir computing unit in the optical domain.

According to embodiments, systems that operate according to the reservoir computing paradigm have reservoir connections with weights that are set at the beginning of a learning operation and that do not change during the learning operation, while only output connections of the reservoir system are trained during the training operation.

Hence according to a further embodiment, the neuromorphic network comprises one or more input nodes, one or more output nodes and a plurality of output connections between the optical reservoir nodes and the one or more output nodes. One or more of the output connections comprise weighting elements that can be adjusted during a training process. According to a preferred embodiment the output nodes, the plurality of output connections and the weighting elements operate also in the optical domain. In other words, optical output connections, optical weighting elements and optical output nodes are provided.

According to such an embodiment, only the output connections of the reservoir system are configured to be weighed and trained for a desired detection target, while the reservoir connections and reservoir nodes have a fixed state/weight during the training. The training may use a software algorithm to perform the training, such as providing information about how to adjust the weights of the optical weighting elements. The resulting trained state of the reservoir system is the encoded in the hardware, i.e. in the weighting elements, preferably in a non-volatile way.

According to an embodiment, the optical neuromorphic network comprises a plurality of output layers. Each of the plurality of output layers is configurable to be trained on performing a classification according to different classification criteria. The classification criteria may be e.g. the particle size and/or the particle concentration of elements to be detected. The plurality of output layers may be formed by one or more reservoir systems.

According to embodiments, nodes and connections of the optical reservoir system and in particular the optical weighting elements may comprise materials whose optical properties can be modified permanently, but changeably, such that a change may be long term. This can be achieved through stimuli applied to the respective tunable element, in particular the optical weighting elements, during the training process. It should be noted that generally according to embodiments the reservoir system may be trained at any level. Preferably the weighting is performed at the level of the output connections only, as described above. The stimuli may be optical, electrical, thermal, mechanical, magnetic, etc., and may depend on the material of the nodes and/or connections and in particular of the material of the optical weighting elements that are used to form the network.

According to an embodiment, the optical neuromorphic network comprises one or more nonlinear optical elements.

The nonlinear optical elements may be e.g. optical amplifiers, detectors, or optical attenuation elements.

According to an embodiment, the optical coupling structure comprises one or more optical waveguides.

According to an embodiment, the interaction region comprises a circular region having a circular shape. The circular region is surrounded by at least one waveguide configured to illuminate the interaction region and by at least one waveguide to collect the transmitted parts of the input signal.

Such an embodied interaction region provides a flexible and efficient solution to provide the optical input signal to the interaction region and to collect the transmitted parts of the optical input signal that have interacted with the analyte.

According to an embodiment, the sensor is configured to process a plurality of different wavelength. This further enhances the possible processing parameters of the sensor and may improve the detection capabilities.

According to an embodiment, the sensor comprises a plurality of interaction regions.

This may further enhance the detection capabilities of the sensor. E.g. each of the interaction regions may be adapted for a specific purpose, e.g. to detect a specific particle or a specific particle size.

According to an embodiment, a first interaction region may be used as a reference region, comprising e.g. a liquid with a fixed distribution of particles, and a second interaction region may be used as sensing region, e.g. for sensing an unknown solution According to an embodiment, the sensor comprises a plurality of optical reservoir systems.

According to such an embodiment, each of the optical reservoir systems may be e.g. trained for a specific purpose, e.g. to detect a specific particle or a specific particle size.

According to an embodiment, the interaction region comprises a microfluidic channel. Furthermore, the illumination source is configured to illuminate at least a part of the microfluidic channel.

The microfluidic channel may be e.g. configured to carry the analyte in a dissolved form in a fluidic medium. The term fluidic medium shall encompass liquids and gases. According to embodiments, the walls/surrounding materials confining the microfluidic channel may comprise silicon oxide, silicon nitride, polymers, silicon, III/V materials and/or functional oxides such as BaTiO3.

According to an embodiment, the interaction region comprises a waveguide structure and a surface or bulk of the waveguide structure is configured to interact with the analyte. This embodiment may be in particular useful for the detection of gases.

According to an embodiment, a surface of the interaction region may be functionalized as to provide specific adsorption sites for molecules to be detected. If a respective molecule is then present in the interaction region, it will be adsorbed by the adsorption sites. This in turn changes the optical behavior/transmission characteristic of the waveguide and hence the transmission of the optical input signal which can be detected by the optical sensor.

According to an embodiment, the sensor is configured to use static light scattering, dynamic light scattering and/or absorption spectroscopy to analyze the analyte.

These are well-established methods which can be used to employ efficient and reliable detection/analysis schemes in dependence on the respective detection/analysis task.

According to an embodiment, the illumination source is a broadband illumination source. According to other embodiments, the optical transmitter may operate at one or more single wavelengths/emission peaks or may comprise an illumination source whose wavelength can be tuned. According to other embodiments, the illumination source may change the spectrum in time, or be modulated.

According to an embodiment, the sensor is configured such that the transmitted parts of the optical input signal have a different spectrum than the optical input signal.

Such an embodied sensor may use e.g. Raman spectroscopy or fluorescence.

According to another aspect of the invention, a method for analyzing an analyte by an optical sensor is provided. The method comprises steps of illuminating, by an illumination source, an interaction region comprising the analyte with an optical input signal and collecting, by an optical coupling structure, transmitted parts of the optical input signal from the interaction region. The method comprises further steps of forwarding, by the optical coupling structure, the transmitted parts of the optical input signal to an optical neuromorphic network and receiving and processing the transmitted parts of the optical input signal in the optical domain by the optical neuromorphic network.

Embodiments of the invention will be described in more detail below, by way of illustrative and non-limiting examples, with reference to the accompanying drawings.

BRIEF DESCRIPTION OF THE DRAWINGS

FIG. 5 shows a schematic illustration of a side view of an interaction region according to another embodiment of the invention;

FIG. 6 shows a schematic illustration of an interaction region having multiple illumination sources.

DETAILED DESCRIPTION

Definitions:

Neuromorphic networks are widely used in pattern recognition and classification, with many potential applications from fingerprint, iris, and face recognition to target acquisition, etc. The parameters (e.g., 'synaptic weights') of the neuromorphic networks can be adaptively trained on a set of patterns during a learning process, following which the neuromorphic network is able to recognize or classify patterns of the same kind.

A key component of a neuromorphic network is the 'synapse,' at which weight information is stored, typically as a continuous-valued variable.

Neuromorphic networks may be used for several types of learning. For the optical sensor according to embodiments of the invention, a "supervised learning approach" may be favorably used. With such a supervised learning approach a set of (input, desired output) pairs is provided to the neuromorphic network, one at a time, and a learning algorithm finds values of the "weights" (the adjustable parameters of the neuromorphic network) that minimize a measure of the difference between the actual and the desired outputs over the training set. If the neuromorphic network has been well trained, it will then process a novel (previously unseen) input to yield an output that is similar to the desired output for that novel input. That is, the neuromorphic network will have learned certain patterns that relate input to a desired output. Furthermore, it may generalize this learning to novel inputs. More particularly, optical sensors according to embodiments may be trained with a plurality of input sets of elements/analytes that shall be detected/analyzed by the optical sensor. Thereby the sensor learns the respective transmission characteristics of these elements/analytes for optical input signals illuminating the interaction region.

Figure 1:
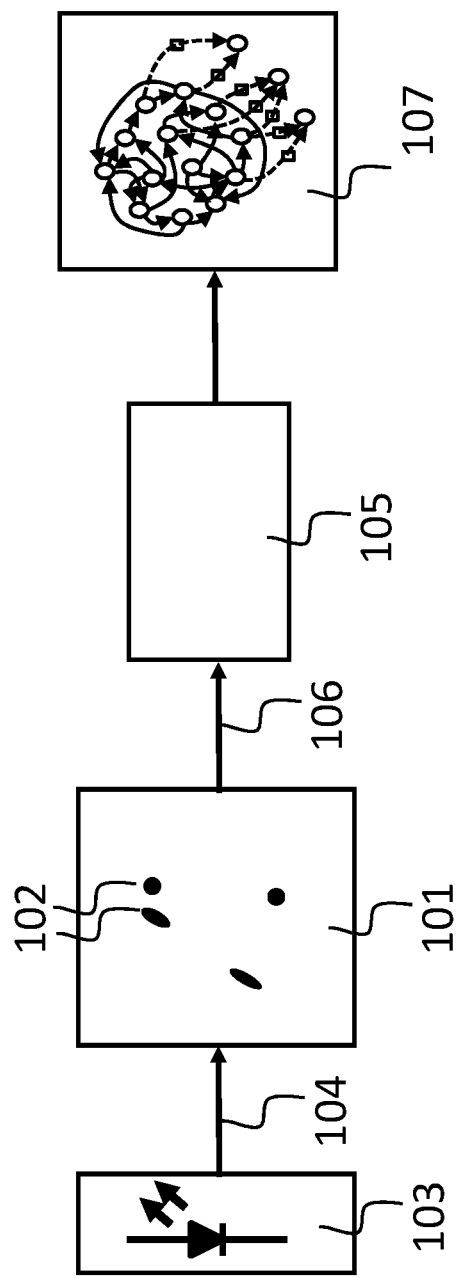
FIG. 1 shows a schematic block diagram of an optical sensor according to an embodiment of the invention.

FIG. 1 shows a schematic block diagram of an optical sensor 100 according to an embodiment of the invention.

The optical sensor 100 comprises an interaction region 101 that comprises an analyte 102 that shall be detected by the optical sensor 100. The analyte 102 may encompass all kind of elements such as e.g. particles, molecules, chemical substances, plasma or gases. The optical sensor 100 further comprises an illumination source 103 that in operation illuminates the interaction region 101 with an optical input signal 104.

According to embodiments, the illumination source 103 may be a broadband illumination source. According to embodiments, the illumination source may emit in the mid infrared (IR) range, i.e. in a range between 3μm and 8μm. According to other embodiments, the illumination source may emit in the near IR range, i.e. in a range between 0.7 and 3 μm and/or in the visible range, i.e. in a range between 0.4μm and 0.7μm According to some embodiments, the illumination source may operate at a single wavelength. According to other embodiments, the wavelength of the illumination source may be tuned.

The illumination source 103 may be a coherent or an incoherent light source, e.g. a laser or a LED. The illumination source 103 may be an embedded illumination source fabricated e.g. from III/V or other gain materials. According to some embodiments, the illumination source 103 may emit the light directly into the interaction region 101. According to other embodiments, the light source 103 may comprise a waveguide or another optical coupling structure to couple the light generated by the illumination source into the interaction region 101. According to an embodiment, the illumination source 103 may comprise a diffraction pattern to couple the optical input signal 104 into the interaction region 102. The diffraction pattern may be e.g. a grating coupler. The optical input signal 104 may illuminate the interaction region 101 from any direction that is suitable for the specific geometry of the interaction region 102. E.g., the illumination source 103 may illuminate the interaction region 101 from the top, from the side, from the bottom, or any combination thereof.

The optical sensor 100 comprises further an optical coupling structure 105 that collects transmitted parts 106 of the optical input signal 104 from the interaction region 101 and forwards the transmitted parts 106 to an optical neuromorphic network 107. The transmitted parts 106 may be any parts of the optical input signal 104 that can be collected by the optical coupling structure 105 and hence arrive at the optical coupling structure 105. The optical input signal may e.g. be scattered, reflected, distracted and/or absorbed by the analyte 102 within the interaction region 101. The scattered, reflected and/or distracted parts of the optical input signal 104 that are collected by the optical coupling structure 105 are denoted as transmitted parts 106 of the optical input signal 104.

The optical neuromorphic network 107 is directly optically connected to the optical coupling structure 106 and hence receives the transmitted parts 106 of the optical input signal 104 in the optical domain. Accordingly, the optical neuromorphic network 107 can process the transmitted parts 106 in the optical domain.

The optical neuromorphic network 107 can be trained on performing a classification of the analyte 102. The training may be in particular performed as supervised learning as described above. The optical neuromorphic network 107 can also be trained on performing a forecast of one or more properties of the analyte 102, such as a gas concentration.

According to embodiments, the neuromorphic network 107 can be used to detect changes in the transmitted part 106 of the optical input signal. Such an embodied optical sensor 100 is not only sensitive to constant properties such as particle size and gas concentration of the analyte 102, but also to certain temporal patterns and/or changes. E.g., the output of the neuromorphic network 107 may indicate if a fluctuation of the signal with a certain frequency appears, or if a sudden drop/increase/change in the transmission spectrum appears.

The sensor 100 may be embodied according to various detection principles. According to exemplary embodiments, static light scattering, dynamic light scattering or absorption spectroscopy may be used to analyze and/or detect the analyte 102.

Figure 2:
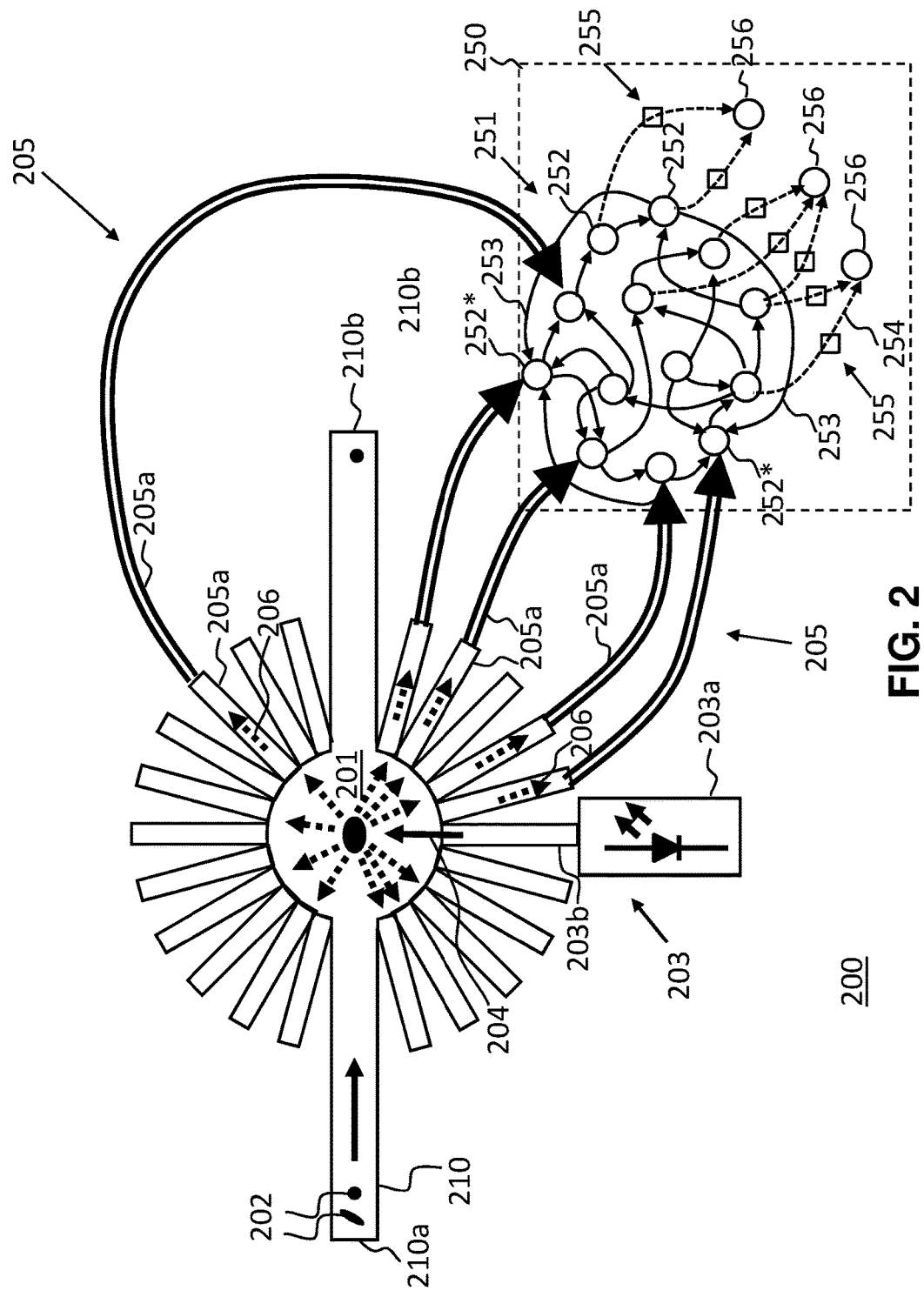
FIG. 2 shows a schematic illustration of a top view of an optical sensor according to another embodiment of the invention comprising an interaction region formed by a microfluidic channel.

FIG. 2 shows a schematic illustration of an optical sensor 200 according to another embodiment of the invention. The optical sensor 200 comprises an interaction region 201 that comprises as analyte elements 202 such as particles or gases that shall be detected by the optical sensor 200. The interaction region 201 has a circular shape and is surrounded by a plurality of waveguides. The interaction region 201 comprises a microfluidic channel 210 that is adapted to transport or carry the elements 202 that shall be detected. The elements 202 may be dissolved in a fluidic medium of the microfluidic channel 210. The microfluidic medium may be e.g. water or another microfluidic medium that is suitable to carry the respective elements 202 to be detected. The walls of the microfluidic channel 210 may comprise or consist of silicon oxide, silicon nitride, polymers, silicon, III/V materials or functional oxides such as BaTiO3. The microfluidic channel 210 may have an inlet at a side 210a of the microfluidic channel 210 and an outlet at an opposite side 210b of the microfluidic channel 210.

The microfluidic medium with the elements 202 to be detected may be supplied at the end 210a of the microfluidic channel 210 and conveyed away at the end 210b.

The sensor 200 comprises an illumination source 203. The illumination source 203 comprises an optical transmitter 203a, e.g. a laser, to generate an optical input signal 204 and a waveguide 203b to guide the optical input signal 204 from the optical transmitter 203a to the interaction region 201. The illumination source 203 illuminates a part of the microfluidic channel 210, namely the interaction region 201.

The optical sensor 200 comprises an optical coupling structure 205 comprising a plurality of waveguides 205a that are arranged around the interaction region 201. The waveguides 205a collect transmitted parts 206 of the optical input signal 204 from the interaction region 201 and forward the transmitted parts 206 to an optical neuromorphic network 250. According to the embodied optical sensor 200, the optical neuromorphic network 250 is embodied as an optical reservoir system 250. As in the embodiment of FIG. 1, the transmitted parts 206 may be any parts of the optical input signal 204 that have been collected and arrived at the optical coupling structure 205. It should be noted that for ease of illustration not all waveguides 205a of FIG. 2 are shown with a connection to the optical reservoir system 250, but only a subset of the optical waveguides 205a. However, according to embodiments all of the waveguides 205a may be connected to the optical reservoir system 250. Furthermore, according to another embodiment some of the waveguides 205a may be connected to other not shown neuromorphic networks or optical reservoir systems. According to embodiments, one or more of the waveguides 205a may be connected to multiple neuromorphic reservoirs. Furthermore, optical amplification structures may be provided in the waveguides 205a to enhance the signal, e.g. by a semiconductor optical amplifier (SOA).

The optical reservoir system 250 is directly optically connected to the waveguides 205a and hence receives the transmitted parts 206 of the optical input signal 204 in the optical domain. Accordingly, the optical reservoir system 250 can process the transmitted parts 206 in the optical domain.

The optical reservoir system 250 comprises an optical reservoir 251 comprising a plurality of optical reservoir nodes 252 and a plurality of optical reservoir connections 253 between the optical reservoir nodes 252. The optical reservoir connections 253 are illustrated with solid lines. Some of the optical reservoir nodes 252 are directly connected to the optical waveguides 205a and serves as input nodes of the optical reservoir system 250, e.g. the input nodes denoted with 252*. The input nodes 252* form an input layer.

The optical reservoir system 250 comprises further a plurality of optical output connections 254 between one or more of the optical reservoir nodes 252 and optical output nodes 256. One or more of the optical output connections 254 comprise optical weighting elements 255, which can be adjusted during a training process. More particularly, the optical reservoir system 250 can be trained to perform a classification of the elements 202 that shall be detected. According to embodiments, the weights of the optical reservoir connections 253 are fixed during the training process, i.e. they do not change during the training process. On the contrary, the weights of the output connections 254 will be trained and hence may be changed during the training process by the optical weighting elements 255. The optical output connections 254 are illustrated with dashed lines.

Hence, according to the above described embodiment the training process of the optical reservoir system 250 will only change the weights of an output layer formed by the optical output nodes 256 and the output connections 254 comprising the optical weighting elements 255. However, the weights of the reservoir connections 253 within the optical reservoir 251 itself will remain fixed and will not change during the training/learning process.

The output nodes 256 deliver an optical output signal, which can be converted into the electrical domain by suitable converters as known to the skilled person in the art. The converted output signals may then be further processed in the electrical domain by suitable hardware or software processing means. The adjustment of the weights of the optical weighting elements 255 may be also done in software or hardware. More particularly, according to embodiments, a hardware control circuit with additional control software running on it may receive the output signals of the output nodes 256 during the training process and may adjust the weights of the optical weighting elements by applying electrical control signals to the optical weighting elements 255. The optical weighting elements 255 may be e.g. embodied as optical attenuators or optical amplifiers. During the training process, certain states of the reservoir system may be assessed. In particular, with some learning algorithms, the state of the output connections 254 after the weighting elements 255 might be needed. Therefore, parts of the optical signal might be split to a dedicated detector and fed to the respective learning algorithm during the training process.

The optical reservoir system 250 comprises some nonlinear signal transformation elements in the reservoir before the weighting elements 255. According to an embodiment, these nonlinear signal transformation elements may be implemented by the optical reservoir nodes 252, or a subset of the optical reservoir nodes 252.

Accordingly, the optical reservoir system 250 may be operated according to the reservoir computing paradigm.

While according to this embodiment the conversion from the optical domain to the electrical domain is performed at the optical output nodes 256, this conversion may be done earlier according to other embodiments. More particularly, according to some embodiments, the conversion to the electrical domain may be already performed at the reservoir nodes 252 that are connected to the output connections 254. According to such an embodiment, the output connections 254 are embodied as electrical output connections, the weighting elements 255 are embodied as electrical weighting elements and the output nodes 256 are embodied as electrical output nodes. However, it should be noted that also according to such an embodiment the optical reservoir 251 itself with the reservoir connections 253 and the reservoir nodes 252 are still in the optical domain only.

As a result, the output connections 254 are trained output connections forming a trained or controlled layer with respect to weighting such that the neuromorphic network/reservoir system 250 can compute desired results, even with unknown inputs. For example, the neuromorphic network/reservoir system 250 may be configured with an output layer that is controlled for weighting that when a known input is supplied at the input nodes/input layer, a known output is generated at the output nodes/output layer. And, when an unknown input is supplied to the reservoir system 250, the output at the output nodes 256 may be robust, reliable, and accurate.

More particularly, the input layer of the reservoir system 250 receives the transmitted parts of the optical input signal corresponding to elements to be identified or classified. This information is then processed by the optical reservoir system 250 and the optical reservoir system 250 supplies information identifying or classifying the elements to the output nodes 256.

As described herein, weights or weighting may be an altering or modification of a transmission through the output connections 254. That is, the transmission of a pulse through the output connections 254 may be controlled to provide a greater or lesser weight based on the training of the network, thus having certain connections be stronger while others are weaker. For example, a waveguide can be used where the transmission is tuned during training. In such an example, the output information may be encoded in the amplitude of an optical signal in the waveguide. The optical signal can be superimposed with the signal of other waveguides, and such a system can encode information about a class in different amplitudes.

As another example, weighting may be achieved in a routing change process. For example, one or more Mach-Zehnder interferometers may be used where the phase of the optical mode in one arm of the interferometer is shifted. A signal of a waveguide can be transferred from one waveguide to another waveguide. Such a configuration may enable routing between different or multiple connections. As a result, the training would result in a routing path of input signals to different output waveguides to achieve the desired outcome during the training.

According to embodiments the optical reservoir system may 250 comprise a plurality of output layers that may be formed by different sets of the output nodes 256. Each of the plurality of output layers may be trained on performing a classification according to different classification criteria, e.g. particle size and particle concentration.

Those of skill in the art will appreciate that other configurations of a neuromorphic network and an optical reservoir system are possible. For example, a reservoir of a neuromorphic network may be configured with virtual reservoir nodes. Time multiplexing may be used in such configurations.

Accordingly, the optical reservoir system 250 employs reservoir computing by a reconfigurable reservoir or network. Further, by adjusting the weights of the various connections in the network, the network may be tuned to operate at different stable operation points, and thus may be re-configurable to each of the stable operation points. As described herein, according to embodiments the nodes or neurons of the reservoir system may enable hardware tuning of output, input, and reservoir weight. Furthermore, according to embodiments weighting and training of the neuromorphic network may be performed at the hardware level. The training may use a software algorithm to perform the training, such as providing information about how to adjust the hardware weights. The resulting trained state of the network is encoded non-volatilely in the hardware (i.e., in the nodes and the connections between them), rather than being a software weight that is applied during the computing process.

In some embodiments, this may be achieved by constructing the reservoir system from materials whose optical properties can be modified permanently, but changeably, such that a change in one of the nodes and/or layers may be long term and achieved through stimuli, resulting in a neuromorphic network that is trained at any level and internally, not relaying on any external software and/or algorithms. The stimuli may be optical, electrical, thermal, mechanical, magnetic, etc., and may depend on the material of the nodes and/or connections that are used to form the network.

In accordance with an embodiment of the present disclosure, a silicon photonics chip is configured as an optical sensor comprising an optical reservoir system. At each or part of the nodes in the reservoir system, a structure, e.g. comprising waveguides, resonators, or interferometers having variable transmission may be used. The transmission function of the resonator may be varied as it is based on materials having a strong electro-optic coefficient or more generally on materials whose optical properties show a dependence on optical or electrical stimuli. Various non-limiting examples are materials where the real part refractive index of the material can be substantially modified upon the application of an electrical field (e.g., materials with a strong Pockels effect) and/or where the imaginary part of the refractive index can be modified by an electric field/current (e.g., materials with a crystalline phase transition: VO2, PCM-materials, etc.). Further, in accordance with some non-limiting embodiments, the change of the optical properties in the material might be caused by optical stimuli (e.g., for phase transitions, photorefractive effect, etc.). Those of skill in the art will appreciate that other materials may be used, other than silicon. For example, III-V semi-conductor materials may be used, without departing from the scope of the present disclosure.

According to further embodiments, delay lines may be provided within one or more waveguides 205a of the coupling structure 205. This may spread the transmitted parts 206 of the input signal over time.

According to a further embodiment, the optical reservoir system 250 may comprise delay lines for spreading out the optical signal that is processed for short ranges, e.g. nanoseconds.

According to a further embodiment, the optical reservoir system 250 may comprise materials such as $VO_2$ to cause optically induced phase transitions with long relaxation times to reach longer time scales of e.g. more than 1 μs.

Figure 3:
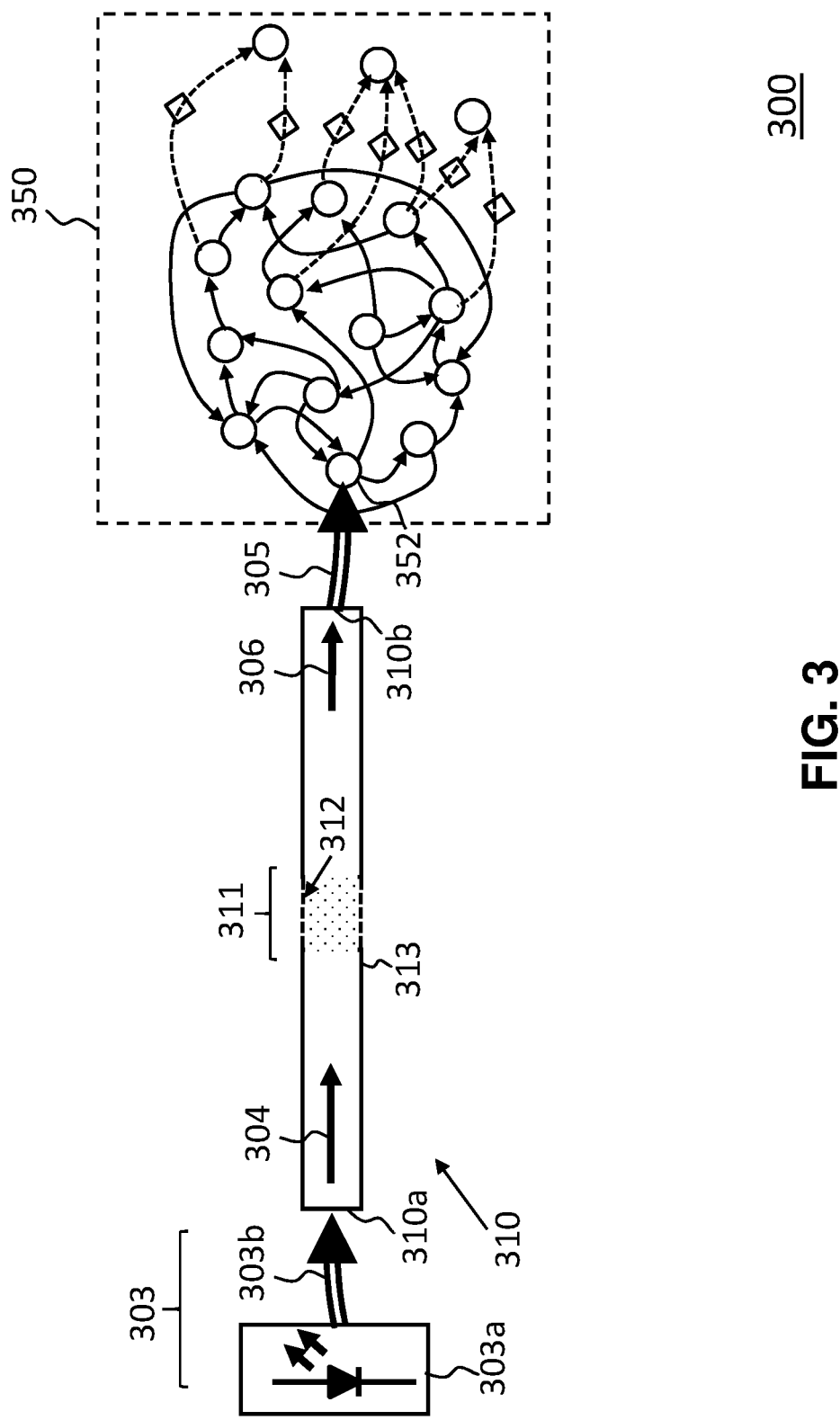
FIG. 3 shows a schematic illustration of an optical sensor according to another embodiment of the invention comprising an interaction region formed by a waveguide.

FIG. 3 shows a schematic illustration of an optical sensor 300 according to another embodiment of the invention.

The optical sensor 300 comprises a waveguide structure 310. A part of the waveguide structure 310 forms an interaction region 311. In the interaction region 311 the waveguide structure 310 has a porous surface 312 which is indicated in FIG. 3 by the dashed lines. This embodiment is in particular suitable to detect gases, but also suitable fluids may be detected. More particularly, gases or fluids to be detected may enter the waveguide structure 310 through the porous surface 312. According to some embodiments, a detectable gas may then distribute within the waveguide structure 310 and influence thereby the transmission behavior of the waveguide structure 310, in particular within the interaction region 311. According to another embodiment, the surface 312 or bulk 313 of the waveguide structure 310 may interact with elements to be detected. According to embodiments, the surface 312 of the interaction region may be functionalized and provide specific adsorption sites for specific molecules to be detected.

The sensor 300 comprises an illumination source 303. The illumination source 303 comprises an optical transmitter 303a to generate an optical input signal 304 and a waveguide 303b to guide the optical input signal 304 from the optical transmitter 303a to the waveguide structure 310. According to other embodiments, the optical transmitter 303a may also be arranged directly within the waveguide structure 310. The optical input signal 304 is transmitted from a left end 310a of the waveguide structure 310 to a right end 310b of the waveguide structure 310. During this transmission, the optical input signal 304 interacts with elements to be detected within the interaction region 311 as described above. E.g. if a gas has entered the interaction region 311 through the porous surface 312, the optical input signal may be reflected, distracted or scattered by the respective gas. Or, if the surface 312 has been functionalized, the gas may interact with the surface 312 and thereby cause a change of the material properties of the surface 312 which in return changes the transmission behavior of the waveguide structure 310 for the optical input signal 304. The transmitted parts 306 of the optical input signal are fed via an optical coupling structure 305 to an optical reservoir system 350 that processes the transmitted parts 306 in the optical domain. According to this embodiment, the waveguide structure 305 may only comprise a single waveguide that optically connects the waveguide structure 310 with only one reservoir node 352 of the optical reservoir system 350. The optical reservoir system 350 may be embodied in the same or a similar way as the optical reservoir system 250 as described with reference to FIG. 2.

Figure 4:
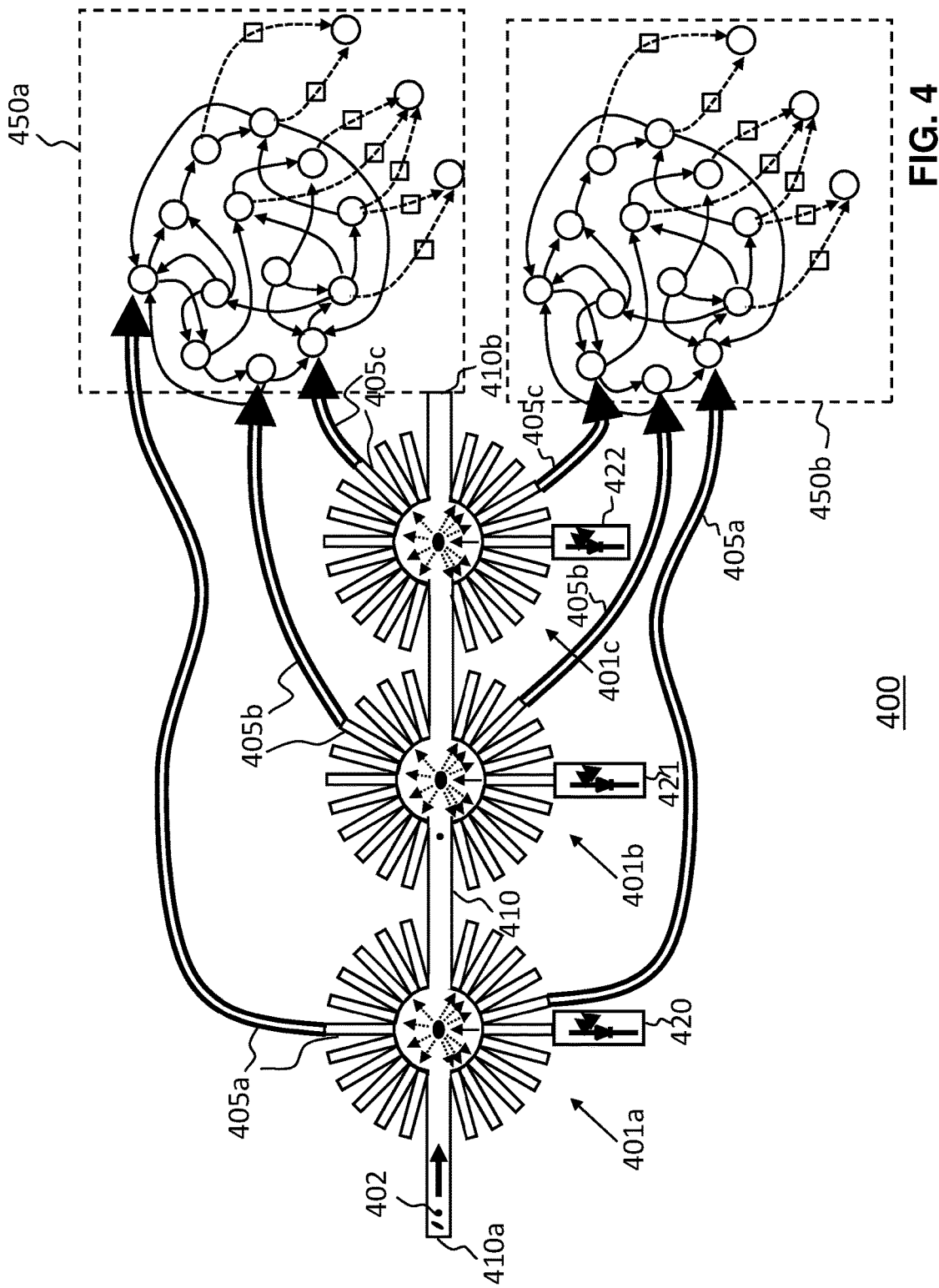
FIG. 4 shows a schematic illustration of a top view of an optical sensor according to another embodiment of the invention comprising a plurality of interaction regions and a plurality of optical reservoir systems.

FIG. 4 shows a schematic illustration of an optical sensor 400 according to another embodiment of the invention. The optical sensor 400 comprises a microfluidic channel 410 that is adapted to transport or carry as analyte elements 402 that shall be detected. The elements 402 may be dissolved in a fluidic medium of the microfluidic channel 410 as described above with reference to FIG. 2. The optical sensor 400 comprises three interaction regions 401a, 401b and 401c. The interaction regions 401a, 401b and 401c have all a circular shape and are each surrounded by a plurality of waveguides. The microfluidic channel 410 has an inlet at a side 410a of the microfluidic channel 410 and an outlet at an opposite side 410b of the microfluidic channel 410.

Each of the interaction regions 401a, 401b and 401c is illuminated by an illumination source 420, 421 and 422 respectively. The illumination source 420 comprises an optical transmitter to generate an optical input signal and a waveguide to guide the optical input signal from the optical transmitter to the interaction region 401a. Likewise, the illumination source 421 comprises an optical transmitter to generate an optical input signal and a waveguide to guide the optical input signal from the optical transmitter to the interaction region 401b. Likewise, the illumination source 422 comprises an optical transmitter to generate an optical input signal and a waveguide to guide the optical input signal from the optical transmitter to the interaction region 401c.

The optical sensor 400 comprises a first optical reservoir system 450a and a second optical reservoir system 450b. Each of the optical interactions regions 401a, 401b and 401c may be coupled to one or both of the optical reservoir systems 450a and 450b.

In FIG. 4 optical coupling structures 405a, 405b and 405c are provided to collect and forward transmitted parts of the respective input signal of the first interaction region 401, the second interaction region 401b and the third interaction region 401c respectively to both of the optical reservoir systems 450a and 450b. It should again be noted that for ease of illustration not all waveguides that are arranged around the respective interaction regions are shown with a connection to the optical reservoir systems 450a and/or 450b. According to embodiments, each of the waveguides may be connected to one of the optical reservoir systems 450a or 450b or to other not shown optical reservoir systems.

FIG. 5 shows a schematic illustration of a side view of an interaction region 501 according to another embodiment of the invention. Such an interaction region 501 may be combined with any of the optical sensors 100, 200, 300 and 400 as described above. The optical interaction region 501 comprises a first part 510 that is embedded in a chip and a second part 511 that is established in a free space manner by air or a liquid. An optical input signal 504 may be fed into the interaction region 501 via an input waveguide 503b that may receive the optical input signal 504 from an optical transmitter 503 integrated into the chip. The optical input signal 504 interacts then with elements 502 that correspond to an analyte and may e.g. be reflected back into one or more of the waveguides of an optical coupling structure 505 which may then forward the reflected parts to an optical reservoir system for further processing in the optical domain as described above.

According to the embodiment as illustrated in FIG. 5, the coupling from the waveguide 503b to free space, both for illumination and detection, is done via butt coupling. According to other embodiments, this coupling may be done by tapering down the waveguide in order to expand the respective mode into free space/the interaction region, or via grating couplers.

FIG. 6 shows a schematic illustration of a top view of an interaction region 601 according to another embodiment of the invention. The interaction region 601 has a circular shape and may be combined with any of the optical sensors 100, 200, 300 and 400 as described above. The optical interaction region 601 comprises a microfluidic channel 610 comprising the interaction region 601. According to this embodiment, the interaction region 601 is illuminated by two different illumination sources 611, 612 which illuminate the interaction region 612 from different angles. The first illumination source 611 comprises an optical transmitter 611a and a waveguide 611b feeding an optical input signal 604a into the interaction region 601. The second illumination source 612 comprises an optical transmitter 612a and a waveguide 612b feeding an optical input signal 604b into the interaction region 601.

The optical input signals 604a, 604b may then interact with elements 602 to be detected/analyzed and may e.g. be reflected back into one or more of the waveguides of an optical coupling structure 605, which may then forward the transmitted parts to an optical reservoir system for processing in the optical domain as described above. The illumination sources 611, 612 may have the same or different emission spectra.

Figure 7:
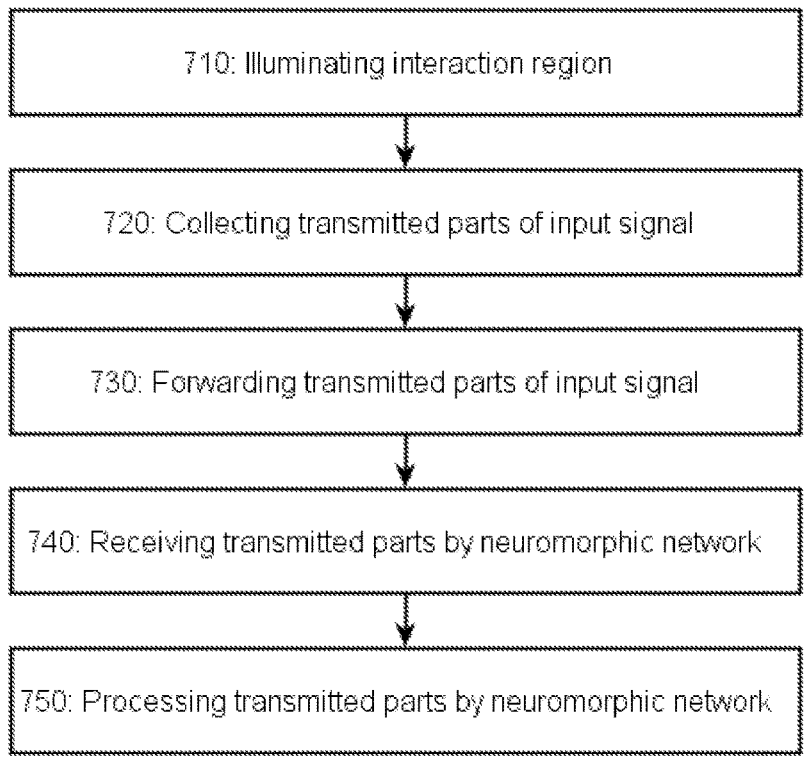
FIG. 7 illustrates method steps of a method for analyzing an analyte by an optical sensor according to embodiments of the invention.

FIG. 7 illustrates method steps of a method for analyzing an analyte, e.g. a method for detecting elements, by an optical sensor, e.g. the optical sensor 100 as described with reference to FIG. 1.

At a step 710, an illumination source, e.g. the illumination source 103 of FIG. 1, illuminates an interaction region, e.g. the interaction region 101 of FIG. 1.

At a step 720, an optical coupling structure, e.g. the optical coupling structure 105 of FIG. 1, collects transmitted parts of the optical input signal from the interaction region 101.

At a step 730, the optical coupling structure 105 forwards the transmitted parts of the optical input signal to an optical neuromorphic network, e.g. the optical neuromorphic network 107 of FIG. 1.

At a step 740, the optical neuromorphic network 107 receives the transmitted parts of the optical input signal from the optical coupling structure 105.

At a step 750, the optical neuromorphic network 107 processes the transmitted parts of the optical input signal in the optical domain.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An optical sensor comprising
   an interaction region configured to comprise an analyte;
   an illumination source configured to illuminate the interaction region with
   an optical input signal;
   an optical coupling structure configured to collect transmitted parts of the optical input signal from the interaction region; and
   an optical neuromorphic network being directly optically coupled to the optical coupling structure and being configured to receive and process the transmitted parts of the optical input signal in the optical domain.

2. An optical sensor as claimed in claim 1, wherein the optical neuromorphic network is configured to be trained on performing a classification of the analyte.

3. An optical sensor as claimed in claim 1, wherein the optical neuromorphic network is an optical reservoir system.

4. An optical sensor as claimed in claim 3, wherein the optical reservoir system comprises
   a plurality of optical reservoir nodes; and
   a plurality of optical reservoir connections between the plurality of optical reservoir nodes.

5. An optical sensor according to claim 4, further comprising
   one or more input nodes;
   one or more output nodes;
   a plurality of output connections between the optical reservoir nodes and the output nodes, wherein one or more of the plurality of output connections comprise weighting elements which can be adjusted during a training process.

6. An optical sensor as claimed in claim 1, wherein the optical neuromorphic network comprises one or more non-linear optical elements.

7. An optical sensor as claimed in claim 1, wherein the optical coupling structure comprises one or more optical waveguides.

8. An optical sensor as claimed in claim 1, wherein the interaction region comprises a circular region having a circular shape, the circular region being surrounded by at least one waveguide configured to illuminate the interaction region and at least one waveguide to collect the transmitted parts of the input signal.

9. An optical sensor as claimed in claim 1, wherein the sensor is configured to process a plurality of different wavelength.

10. An optical sensor as claimed in claim 1, wherein the sensor comprises a plurality of interaction regions.

11. An optical sensor as claimed in claim 1, wherein the sensor comprises a plurality of optical reservoir systems.

12. An optical sensor as claimed in claim 1, wherein the interaction region comprises a microfluidic channel, the illumination source is configured to illuminate at least a part of the microfluidic channel and the microfluidic channel is configured to carry the analyte in a dissolved form in a fluidic medium.

13. An optical sensor as claimed in claim 1, wherein the optical neuromorphic network is configured to perform a forecasting of one or more properties of the analyte.

14. An optical sensor as claimed in claim 1, wherein the interaction region comprises a waveguide structure and wherein a surface or bulk of the waveguide structure is configured to interact with the analyte.

15. An optical sensor as claimed in claim 14, wherein a surface of the interaction region is functionalized as to provide specific adsorption sites for molecules to be detected.

16. An optical sensor as claimed in claim 1, wherein the sensor is configured to use static light scattering, dynamic light scattering and/or absorption spectroscopy to analyze the analyte.

17. An optical sensor as claimed in claim 1, wherein the optical neuromorphic network comprises a plurality of output layers, wherein each of the plurality of output layers is configurable to be trained on performing a classification according to different classification criteria.

18. An optical sensor as claimed in claim 1, wherein the illumination source is a broadband illumination source.

19. An optical sensor as claimed in claim 1, wherein the sensor is configured such that the transmitted parts of the optical input signal have a different spectrum than the optical input signal.

* * * * *